US009422349B2

(12) United States Patent
Jung et al.

(10) Patent No.: US 9,422,349 B2
(45) Date of Patent: *Aug. 23, 2016

(54) N-TERMINAL MODIFIED EXENDIN-4

(75) Inventors: Sung Youb Jung, Suwon-si (KR); Chang Ki Lim, Suwon-si (KR); Dae Hae Song, Seoul (KR); Sung Min Bae, Seongnam-si (KR); Young Hoon Kim, Seoul (KR); Se Chang Kwon, Seoul (KR); Gwan Sun Lee, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 220 days.

This patent is subject to a terminal disclaimer.

(21) Appl. No.: 12/669,372

(22) PCT Filed: Jul. 16, 2008

(86) PCT No.: PCT/KR2008/004170
§ 371 (c)(1),
(2), (4) Date: Jan. 15, 2010

(87) PCT Pub. No.: WO2009/011544
PCT Pub. Date: Jan. 22, 2009

(65) Prior Publication Data
US 2010/0204451 A1    Aug. 12, 2010

Related U.S. Application Data

(60) Provisional application No. 60/991,155, filed on Nov. 29, 2007.

(30) Foreign Application Priority Data

Jul. 16, 2007  (KR) .................. 10-2007-0071071

(51) Int. Cl.
C07K 14/605 (2006.01)
A61K 38/26 (2006.01)
C07K 14/46 (2006.01)
C07K 14/575 (2006.01)

(52) U.S. Cl.
CPC .......... *C07K 14/46* (2013.01); *A61K 38/26* (2013.01); *C07K 14/57563* (2013.01); *C07K 14/605* (2013.01)

(58) Field of Classification Search
None
See application file for complete search history.

(56) References Cited

U.S. PATENT DOCUMENTS

| 5,424,286 | A  | 6/1995  | Eng |
| 5,545,618 | A  | 8/1996  | Buckley et al. |
| 6,573,237 | B2 | 6/2003  | Rinella, Jr. |
| 6,956,026 | B2 | 10/2005 | Beeley et al. |
| 7,157,555 | B1 | 1/2007  | Beeley et al. |
| 7,220,721 | B1 | 5/2007  | Beeley et al. |
| 8,476,230 | B2 * | 7/2013 | Song et al. ............... 514/6.9 |
| 2001/0047084 | A1 | 11/2001 | Knudsen et al. |
| 2003/0199672 | A1 | 10/2003 | Knudsen et al. |
| 2004/0266683 | A1 * | 12/2004 | Hathaway et al. ........... 514/12 |
| 2005/0037958 | A1 | 2/2005 | Young et al. |
| 2008/0119390 | A1 | 5/2008 | Mozes |

FOREIGN PATENT DOCUMENTS

| EP | 0 708 179 B1 | 12/2004 |
| EP | 1 938 831 A1 | 7/2008 |
| EP | 2390265 B1 | 11/2013 |
| JP | 1996-245696 A | 9/1996 |
| JP | 2002-507188 A | 3/2002 |
| JP | 2002-523466 A | 7/2002 |
| JP | 2005-524658 A | 8/2005 |
| KR | 10-2004-0038901 A | 5/2004 |
| KR | 10-2007-0042162 A | 4/2007 |
| WO | 98/08873 A1 | 3/1998 |
| WO | 98/30231 A1 | 7/1998 |
| WO | 99/07404 A1 | 2/1999 |
| WO | 00/12116 A1 | 3/2000 |
| WO | 03/072195 A2 | 9/2003 |
| WO | 2006/097538 A1 | 9/2006 |
| WO | 2007/024700 A2 | 3/2007 |
| WO | 2007/063907 A1 | 6/2007 |
| WO | 2008/019147 A2 | 2/2008 |
| WO | 2008-082274 A1 | 7/2008 |

OTHER PUBLICATIONS

Goke et al., "Exendin-4 Is a High Potency Agonist and Truncated Exendin-(9-39)-amide an Antagonist at the Glucagon-like Peptide 1-(7-36)-amide Receptor of Insulin-secreting β-Cells," The Journal of Biological Chemistry, 1993, vol. 268, No. 26, pp. 19650-19655.

Gallwitz et al., "GLP-1-analogues Resistant to Degradation by Dipeptidyl-Peptidase IV in Vitro," Regulatory Peptides, 2000, pp. 103-111.

Siegel et al., "Biological Activity of GLP-1-analogues with N-terminal Modifications," Regulatory Peptides, 1999, pp. 93-102.

Burcelin et al., "Long-Lasting Antidiabetic Effect of a Dipeptidyl Peptidase IV-Resistant Analog of Glucagon-Like Peptide-1," Metabolism, 1999, vol. 48, No. 2, pp. 252-258.

Deacon et al., "Dipeptidyl Peptidase IV Resistant Analogues of Glucagon-like Peptide-1 Which Have Extended Metabolic Stability and Improved Biological Activity," Diabetologia, 1998, vol. 41, pp. 271-278.

(Continued)

*Primary Examiner* — Zachary Howard
(74) *Attorney, Agent, or Firm* — Sughrue Mion, PLLC

(57) ABSTRACT

The present invention relates to an N-terminal amino acid-modified insulinotropic peptide having a high activity, and to a pharmaceutical composition comprising the same. The insulinotropic peptide derivatives according to the present invention exhibit therapeutic effects, which are not observed in native and other insulinotropic peptide analogs. Therefore, the insulinotropic peptide derivatives and the pharmaceutical composition comprising the same according to the present invention can be effectively provided for the treatment of the diseases.

8 Claims, 3 Drawing Sheets

(56) References Cited

OTHER PUBLICATIONS

U.S. Appl. No. 60/055,404, filed Aug. 8, 1997, Beeley et al.
European Search Report issued in corresponding EP Application No. 08778827.9, dated Sep. 28, 2010.
European Patent Office, European Office Action issued in corresponding EP Application No. 11162132.2, dated Oct. 26, 2011.
Japanese Patent Office, Office Action issued in Japanese Patent Application No. 2012-193520 dated Mar. 11, 2014.
Japanese Patent Office, Office Action issued in Japanese Patent Application No. 2012-193521 dated Mar. 18, 2014.
Intellectual Property Office of the Philippines, Communication dated Jun. 26, 2014, issued in counterpart Application No. 2010/500101.
Korean Patent Office, Korean Notice of Patent Grant issued in corresponding KR Application No. 10-2008-0069234, dated Nov. 30, 2012.
Intellectual Property Office of Singapore, Communication dated Oct. 31, 2014, issued in corresponding Singapore Application No. 2012052114.

* cited by examiner

N-TERMINAL MODIFIED EXENDIN-4

TECHNICAL FIELD

The present invention relates to an insulinotropic peptide derivative having an improved insulinotropic activity. In particular, the present invention relates to an N-terminal amino acid-modified insulinotropic peptide having high stability and insulinotropic activity.

BACKGROUND ART

Since peptides tend to be easily denatured due to their low stability, degraded by in-vivo proteolytic enzymes, thus losing the activity, and have a relatively small size, thereby easily passing through the kidney. Accordingly, in order to maintain the blood level and the titer of a medicament comprising a peptide as a pharmaceutically effective component, it is necessary to administer the peptide drug frequently to a patient to maintain desired blood level and titer. However, the peptide drugs are usually administered in the form of injectable preparations, and such frequent administration for maintaining the blood levels of the physiologically active peptides cause severe pain for the patients. To solve these problems, many efforts have been made. As one of such efforts, there has been suggested an approach that transmission through the biological membrane of the peptide drug is increased, and then the peptide drug is transferred into the body by oropharyngeal or nasopharyngeal inhalation. However, this approach is still difficult in maintaining the in-vivo activity of the peptide drug due to the remarkably lower in-vivo transfer efficiency, as compared with injectable preparations.

On the other hand, many efforts have been made to improve the blood stability of the peptide drug, and to maintain the drug in blood at a high level for a prolonged period of time, thereby maximizing the pharmaceutical efficacy of the drug. The long acting preparation of such peptide drug therefore is required to increase the stability of the peptide drug, and to maintain the titers at sufficiently high levels without causing immune responses in patients.

As a method for stabilizing the peptide, and inhibiting the degradation by a proteolytic enzyme, some trials have been performed to modify a specific amino acid sequence which is sensitive to the proteolytic enzyme. For example, GLP-1 (7-37 or 7-36 amide), which functions to reduce the glucose concentration in blood for the treatment of Type 2 diabetes, has a short half-life of the physiological activity of about 4 minutes or less (Kreymann et al., 1987), due to loss of the titers of GLP-1 through the cleavage between the $8^{th}$ amino acid (Ala) and the $9^{th}$ amino acid (Asp) by a dipeptidyl peptidase IV (DPP IV). As a result, various investigations have been made on a GLP-1 analog having resistance to DPP IV, and trials have been made for substitution of $Ala^8$ with Gly (Deacon et al., 1998; Burcelin et al., 1999), or with Leu or D-Ala (Xiao et al., 2001), thereby increasing the resistance to DPP IV, while maintaining its activity. The N-terminal amino acid $His^7$ of GLP-1 is critical for the GLP-1 activity, and serves as a target of DPP IV. Accordingly, U.S. Pat. No. 5,545,618 describes that the N-terminus is modified with an alkyl or acyl group, and Gallwitz, et al. describes that $His^7$ was subject to N-methylation, or alpha-methylation, or the entire His is substituted with imidazole to increase the resistance to DPP IV, and to maintain physiological activity. Whereas the resistance to dipeptidyl peptidase is increased to improve its stability, the $His^7$-modified derivatives are found to have markedly reduced receptor affinity with lower cAMP stimulation at the same concentration (Gallwitz. et al., Regulatory Peptide 79:93-102 (1999), Regulatory Peptide 86:103-111 (2000)).

In addition to GLP-1, exendins are peptides that are found in the venom of glia monster, a lizard common in Arizona and Northern Mexico. Exendin-3 is present in the venom of Heloderma horridum, and exendin-4 is present in the venom of Heloderma suspectum. The exendins have a high homology of 53% with GLP-1 (Goke, et al., J. Bio. Chem., 268:19650-55 (1993)). Exendin-4 reportedly acts at GLP-1 receptors on specific insulin-secreting cells, at dispersed acinar cells from guinea pig pancreas, and at parietal cells from stomach, and the peptide is also said to stimulate somatostatin release and inhibit gastrin release in isolated stomachs. In addition, exendin-3 and exendin-4 were reportedly found to stimulate cAMP production in pancreatic acinar cells, and to stimulate amylase release from pancreatic acinar cells. Since the exendin-4 (U.S. Pat. No. 5,424,686) has a sequence of His-Gly, instead of His-Ala which functions as a substrate of dipeptidyl peptidase in GLP-1, it has resistance to DPP IV, and higher physiological activity than GLP-1. As a result, it had an in-vivo half-life of 2 to 4 hours, which was longer than that of GLP-1. Although the native exendin has an in-vivo increased half-life than GLP-1, its physiological activity is not sufficiently sustained. For example, in the case of a commercially available exendin-4 (exenatide), it needs to be injected to a patient twice a day, which is still difficult for patients.

To improve therapeutic efficacy of the native exendin, trials have been made to prepare its analogs, derivatives and variants. The term "analog or variant" typically refers to a peptide prepared by substitution, deletion or insertion of one or more amino acids into or from the native peptide. The term "derivative" refers to a chemically modified peptide, prepared by alkylation, acylation, esterification, or amidation of one or more amino acids in the native peptide.

Novel exendin agonist compounds are described in PCT Application No. PCT/US98/16387. Claiming priority thereon, a method for reducing food intake using exendin is disclosed in U.S. Pat. No. 6,956,026. In addition, claiming priority on the PCT application, use of exendins and analogs thereof for the reductions of food intake is disclosed in EP0996459, and exendin agonist compounds are disclosed in U.S. Pat. No. 7,157,555. However, they merely disclose several sequences of exendin analogs. Moreover, there is no mention of activity and property with respect to said analogs, which is also not supported by the detailed description.

DISCLOSURE

Technical Problem

Accordingly, the present inventors found that $His^1$-modified exendin derivatives exhibit higher blood stability and insulinotropic activity than a native exendin, thereby completing the present invention.

Technical Solution

It is an object of the present invention to provide insulinotropic peptide derivatives having improved blood stability and insulinotropic activity.

It is another object of the present invention to provide a pharmaceutical composition for the treatment of diabetes, comprising the insulinotropic peptide derivative having improved insulinotropic activity.

BEST MODE

Figure 1:
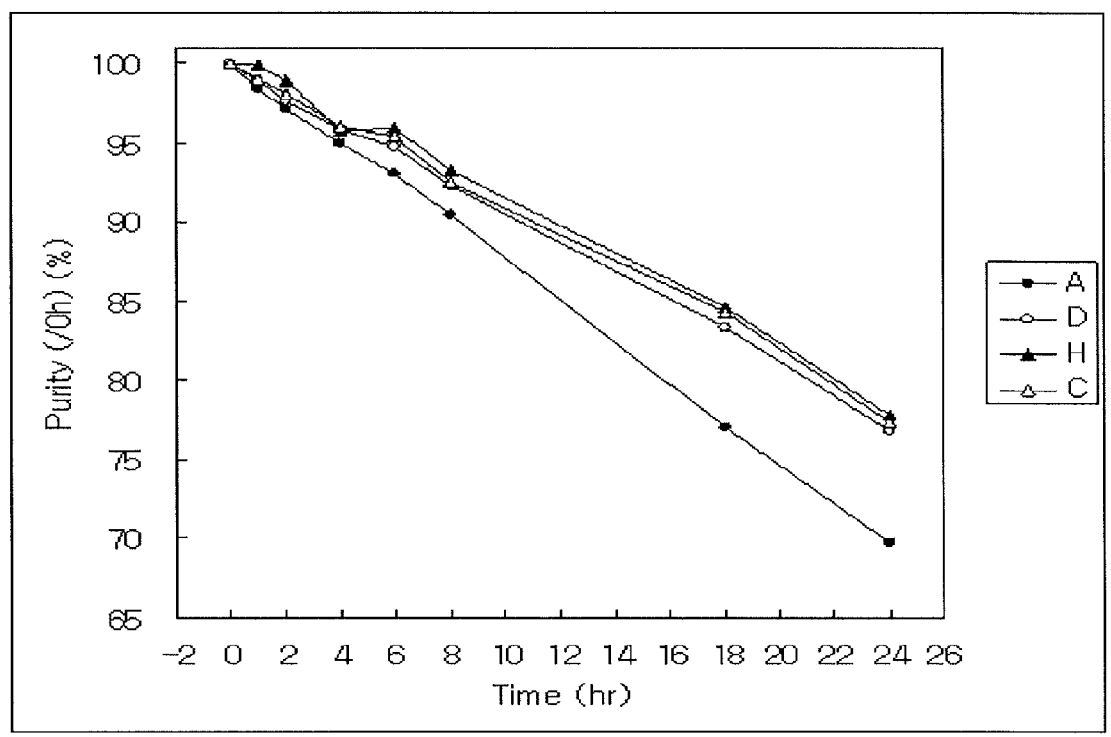
FIG. 1 shows stability of exendin-4 derivatives in serum. A: exendin-4, D: DA-exendin-4, H: HY-exendin-4, C: CA-exendin-4.

In accordance with an aspect, the present invention relates to an insulinotropic peptide derivative having improved blood stability and insulinotropic activity.

The derivative according to the present invention is a derivative having a chemically modified N-terminal histidine residue, or a derivative having a chemically modified amino group of N-terminal histidine residue.

Preferably, the insulinotropic peptide according to the present invention is exendin-4, exendin-3 or derivatives thereof. The term "exendin-4 or exendin-3 derivative" as used herein, refers to a peptide prepared by substituting, deleting and/or adding one or more amino acids of exendin-4 or exendin-3, or a peptide having one or more amino acid residues chemically modified, e.g., alkylation, acylation esterification or amidation, whose activity is equivalent to that of native exendin-4.

As examples of exendin-3 or exendin-4 derivatives, an exendin-4 derivative prepared by deleting C-terminus of exendin-4 or substituting an amino acid of exendin-4 with normatural amino acid, Norleucine is disclosed in WO97/46584. Also, WO99/07404 discloses exendin derivatives whose amino acids are substituted with normatural aminoacids, e.g., pentyl glycine, homoproline or tert-butylglycine, and US2008/0119390 discloses exendin derivatives consisting of shorter amino sequences than the native exendin-4 prepared by deleting some amino acid residues of exendin-4, and prepared by substituting some amino acid residues of exendin-4 with other amino acid residues. These publications are incorporated by references.

Specifically, the present invention may also encompass a derivative thereof with removal of the amino group of N-terminal histidine (desamino-histidyl derivative), a derivative thereof prepared by substitution of the amino group with a hydroxyl group (beta-hydroxyimidazoproionyl derivative), a derivative thereof prepared by modification of the amino group with two methyl residues (dimethyl-histidyl derivative), a derivative thereof prepared by substitution of the amino group with a carboxyl group (beta-carboxylmidazopropionyl derivative), or a derivative thereof with removal of the positive charge of the amino group, in which the alpha carbon of N-terminal histidine residue is removed to remain only the imidazoacetyl group (imidazoacetyl derivative), and other N-terminal amino group modified-derivatives.

Preferably, the present invention provides exendin-4 derivatives having chemically modified N-terminal amino group or amino acid residue, more preferably exendin-4 derivative in which the alpha amino group or alpha carbon of N-terminal histidine residue (the first amino acid of exendin-4) is substituted or removed, and further more preferably desamino-histidyl-exendin-4 (DA-Exendin-4) with removal of the N-terminal amino group, beta-hydroxy imidazopropionyl-exendin-4 (HY-exendin-4) prepared by substitution of the amino group with a hydroxyl group, beta-carboxy imidazopropionyl-exendin-4 (CX-exendin-4) prepared by substitution of the amino group with a carboxyl group, dimethyl-histidyl-exendin-4 (DM-exendin-4) prepared by modification of the amino group with two methyl residues, and imidazoacetyl-exendin-4 (CA-exendin-4) with removal of alpha carbon of N-terminal histidine residue.

Des-amino-histidyl (DA)-Exendin-4

Beta-hydroxy-imidazopropionyl (HY)-Exendin-4

Beta-carboxyl-imidazopropionyl (CX)-Exendin-4 imidazoacetyl (CA)-Exendin-4

Dimethyl-histidyl (DM)-Exendin-4

In accordance with a specific aspect, the present invention relates to an insulinotropic peptide derivative comprising an amino acid of the following Formula 1.

R1-X—R2        <Formula 1> wherein R1 is selected from the group consisting of desamino-histidyl, N-dimethyl-histidyl, beta-hydroxy imidazopropionyl, 4-imidazoacetyl and beta-carboxy imidazopropionyl;

R2 is selected from the group consisting of —NH$_2$, —OH and -Lys,

X is selected from the group consisting (SEQ ID NO: 1)
Gly-Glu-Gly-Thr-Phe-Thr-Ser-Asp-Leu-Ser-Y-Gln-Met- Glu-Glu-Glu-Ala-Val-Arg-Leu-Phe-Ile-Glu-Trp-Leu-Z-

Asn-Gly-Gly-Pro-Ser-Ser-Gly-Ala-Pro-Pro-Pro-Ser, (SEQ ID NO: 2)
Gly-Glu-Gly-Thr-Phe-Thr-Ser-Asp-Leu-Ser-Y-Gln-Met-

Glu-Glu-Glu-Ala-Val-Arg-Leu-Phe-Ile-Glu-Trp-Leu-Z-

Asn-Gly-Gly , and

-continued (SEQ ID NO: 3)
Ser-Asp-Gly-Thr-Phe-Thr-Ser-Asp-Leu-Ser-Y-Gln-Met-

Glu-Glu-Glu-Ala-Val-Arg-Leu-Phe-Ile-Glu-Trp-Leu-Z-

Asn-Gly-Gly-Pro-Ser-Ser-Gly-Ala-Pro-Pro-Pro-Ser;

Y is selected from the group consisting of Lys, Ser, and Arg, and

Z is selected from the group consisting of Lys, Ser, and Arg.

Preferred insulinotropic peptide derivative has Formula 1, wherein R1 is selected from desamino-histidyl, N-dimethyl-histidyl, beta-hydroxy imidazopropionyl, 4-imidazoacetyl and beta-carboxylmidazopropionyl, Y is Lys or Ser, Z is Lys, and R2 is —$NH_2$.

In accordance with another specific aspect, the present invention relates to an insulinotropic peptide derivative comprising an amino acid of the following Formula 2.

R3-X'—R4    <Formula 2>

Wherein R3 is 4-imidazoacetyl;
X is (SEQ ID NO: 1)
Gly-Glu-Gly-Thr-Phe-Thr-Ser-Asp-Leu-Ser-Y-Gln-Met- Glu-Glu-Glu-Ala-Val-Arg-Leu-Phe-Ile-Glu-Trp-Leu-Z-

Asn-Gly-Gly-Pro-Ser-Ser-Gly-Ala-Pro-Pro-Pro-Ser
or (SEQ ID NO: 2)
Gly-Glu-Gly-Thr-Phe-Thr-Ser-Asp-Leu-Ser-Y-Gln-Met-

Glu-Glu-Glu-Ala-Val-Arg-Leu-Phe-Ile-Glu-Trp-Leu-Z-

Asn-Gly-Gly;

R4 is —$NH_2$;

Y is selected from the group consisting of Lys, Ser, and Arg, and

Z is selected from the group consisting of Lys, Ser, and Arg.

In terms of its activity, the chemical modification in the N-terminal histidine residue of exendin-4 has a different effect from that in other insulinotropic peptide GLP-1. The chemical modification in the N-terminal histidine residue of GLP-1, for example, α-methyl-GLP-1, n-methyl-GLP-1, or imi-GLP-1, may be expected to inhibit degradation by dipeptidyl peptidase, thereby increasing the stability, and practical reduction in degradation rate was reported. However, it was also reported that they have relatively reduced receptor affinity with lower cAMP stimulation, as compared to the native GLP-1.

In contrast, since exendin-4 is not cleaved by dipeptidyl peptidase, it would be difficult to predict the effect of the chemical modification in the N-terminal histidine residue on its activity, in particular, its effect on receptor affinity and glucose concentration in blood.

Figure 2:
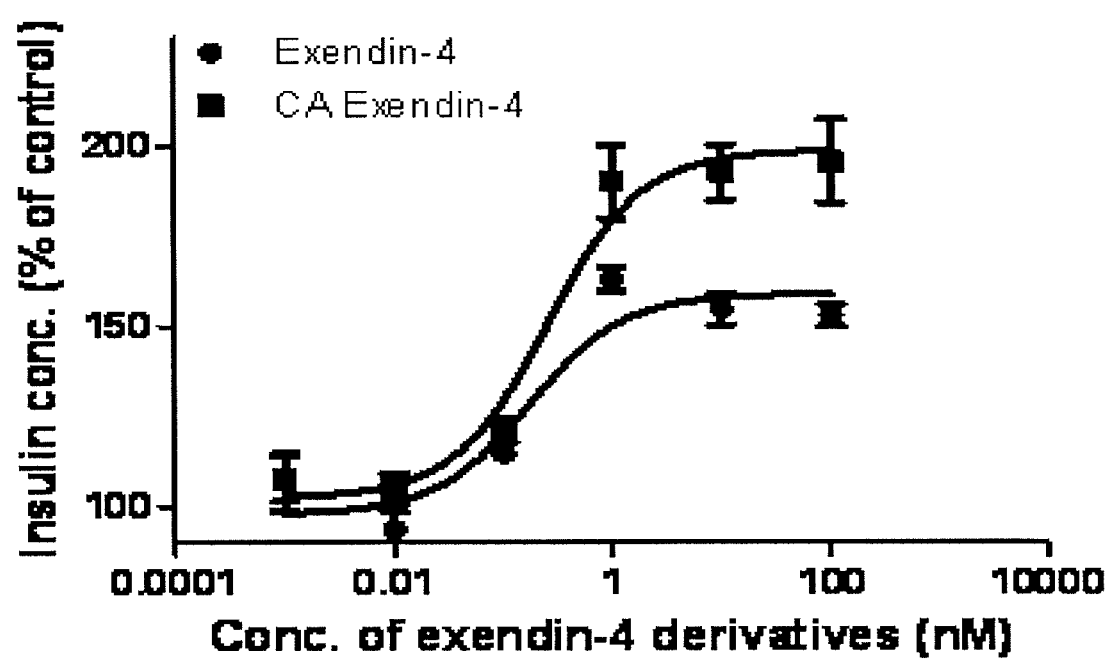
FIG. 2 shows insulinotropic activities of exendin-4, and exendin-4 derivate, CA-exendin 4.
Figure 3:
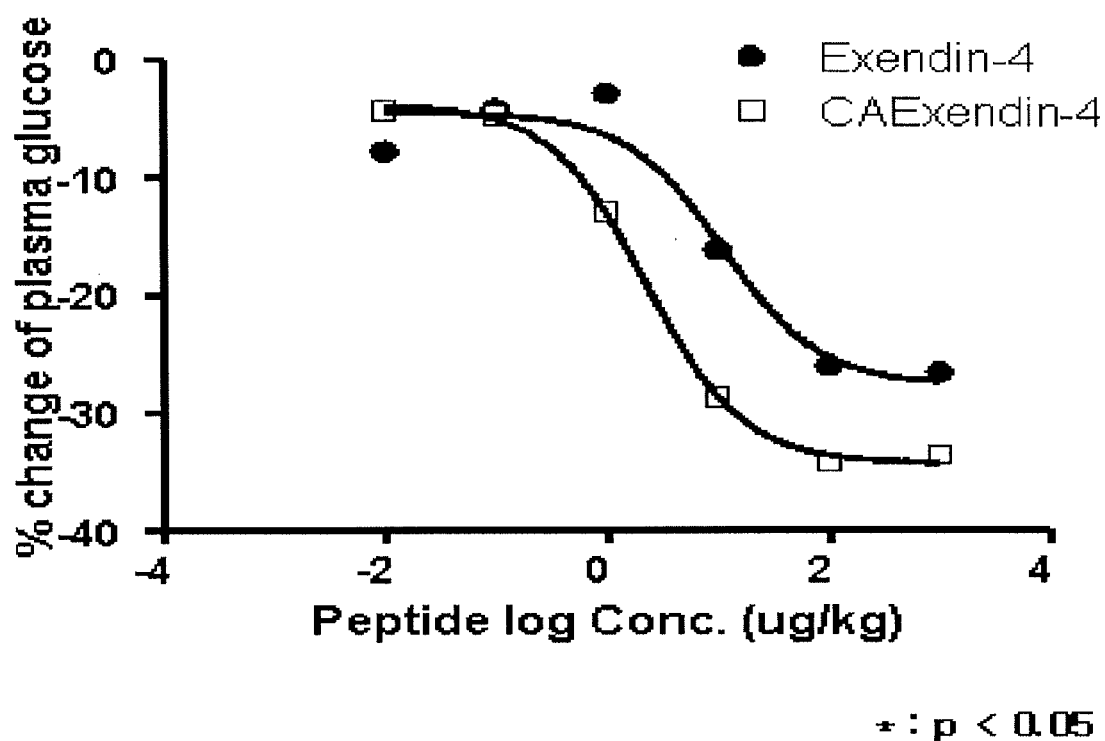
FIG. 3 shows blood glucose lowering effect of exendin-4, and CA-exendin-4 in diabetic model animals.

Accordingly, the present invention provides an exendin-4 derivative having a chemically modified N-terminal histidine residue or having a chemically modified amino group of N-terminal histidine residue, which exhibits unexpected excellent insulinotropic activity compared to native exendin-4. These derivatives exhibited excellent blood stability and insulinotropic activity in vitro, compared to exendin-4 (FIG. 2). Practically, it was found in diabetic db/db mouse that they exhibited an excellent effect of reducing the glucose concentration in blood, compared to the native exendin-4 (FIG. 3). It is thought that the change in net charge due to modification in the amino group of N-terminal histidine residue or the change in size of histidine residue causes a difference in sensitivity to proteolytic attack in blood or affects receptor affinity. However, there is still a need for more extensive molecular studies thereon. Such property is expected to maximize the intrinsic insulinotropic activity of exendin-4, that is, a therapeutic effect on type 2 diabetes, and to induce reduction of food intake, delay in gastric emptying or the like.

The exendin-4 derivatives including desamino-histidyl-exendin-4 (DA-exendin-4), beta-hydroxy imidazopropionyl-exendin-4 (HY-exendin-4), beta-carboxylmidazopropionyl-exendin-4 (CX-exendin-4), dimethyl-histidyl-exendin-4 (DM-exendin-4) and imidazoacetyl-exendin-4 (CA-exendin-4) of the present invention are prepared by removing and substituting the alpha amino group of N-terminal histidine residue or by removing the alpha carbon of N-terminal histidine residue. Therefore, other amino acid sequences are not limited, as long as their activity is maintained. Further, it is obvious to those skilled in the art that the exendin-4 derivatives are modified by a typical method including modification of polymer such as PEG and sugar chain and fusion with albumin or transferrin, so as to enhance their therapeutic effect, being superior to the native exendin-4.

In accordance with another aspect, the present invention provides a pharmaceutical composition for the treatment of diabetes, comprising the insulinotropic peptide derivative.

The term "administration" as used herein means introduction of a predetermined amount of a substance into a patient by a certain suitable method. The conjugate of the present invention may be administered via any of the common routes, as long as it is able to reach a desired tissue. A variety of administration modes are contemplated, including intraperitoneally, intravenously, intramuscularly, subcutaneously, intradermally, orally, topically, intranasally, intrapulmonarily and intrarectally, but the present invention is not limited to these exemplified administration modes. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

The pharmaceutical composition comprising the conjugate of the present invention can further comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, and antiseptics.

The administration frequency and dose of the pharmaceutical composition of the present invention can be determined by several related factors including the types of diseases to be treated, administration routes, the patient's age, gender, weight and severity of the illness, as well as by the types of the drug as an active component. Since the pharmaceutical composition of the present invention has excellent duration of in-vivo efficacy and titer, it can remarkably reduce the administration frequency and dose of pharmaceutical drugs of the present invention.

The insulinotropic derivatives according to the present invention are not disclosed by former inventors, or are broadly disclosed without any specific amino acid sequences and their activities are never compared to those of the native exendin-4, other derivatives and variants. Therefore, it never be expected that exendin-4 derivatives whose alpha amino group or alpha carbon of N-terminus is substituted or deleted exert remarkably excellent activities. Accordingly, the excellent stability in serum and insulinotropic activity of the insulinotropic peptide derivatives according to the present invention maximize a therapeutic effect on type 2 diabetes.

MODE FOR INVENTION

Hereinafter, a better understanding of the present invention may be obtained through the following examples which are set forth to illustrate, but are not to be construed as the limit of the present invention.

Example 1

Plasma Stability of Exendin-4 Derivative

To measure plasma stability of exendin-4 derivatives, each of a native Exendin-4 and Exendin-4 derivatives was exposed to plasma, and the amounts of remaining proteins not denatured were measured by reversed phase HPLC to perform a test for denaturation depending on exposure time.

In the present experiment, to analyze the samples being exposed to plasma, the plasma mixed samples were deproteinised, and then analyzed.

The native exendin-4, desamino-histidyl-exendin-4 (DA-Exendin-4), beta-hydroxy imidazopropionyl-exendin-4 (HY-exendin-4), beta-carboxy imidazopropionyl-exendin-4 (CA-exendin-4), dimethyl-histidyl-exendin-4 (DM-exendin-4), and imidazoacetyl-exendin-4 (CA-exendin-4) were prepared at a concentration of 1 mg/ml, respectively. 200 µl of each exendin-4 derivative sample was mixed with 200 µl of rat serum, and the reaction was performed at 37° C. and at each sampling time. 100 µl of each sample was taken at each time point of 0 hr, 1 hr, 2 hr, 4 hr, 6 hr, 8 hr, 18 hr, and 24 hr. 400 µl of ice-cold methanol was added to 100 µl of the sample to terminate the reaction, followed by vortexing for 20 sec. Each mixture was centrifuged at 15,000 rpm for 30 min, and the supernatant was taken for analysis.

A reversed phase HPLC was performed using a gradient of TFA in ACN as a mobile phase and using a C18 column.

The results were calculated from a ratio (%) of a major peak area of exendin-4 to total peak area, and the result of each derivative at a time point of 0 hr was taken as 100%, resulting in a graph plotting a pattern that the ratio of a major peak area decreases, as exposure time increases.

Up to the time point of 24 hr, whereas the purity of native exendin-4 decreased by about 70%, the purity of three derivatives (D, H, C form) decreased by about 77%, 78%, 77%, respectively (FIG. 1).

Example 2

Measurement of In Vitro Activity of Exendin-4 Derivative

To measure the efficacy of exendin-4 derivatives including desamino-histidyl-exendin-4, their in-vitro cell activity was examined. The native exendin-4 and exendin-4 derivatives were synthesized by American Peptide Corporation. Insulinoma cells or islets of Langerhans, which are generally used for measurement of in-vitro activity of GLP-1, were isolated, and changes in the cAMP production were analyzed upon GLP-1 treatment.

In the present experiment, the in-vitro activity was measured using RIN-m5F (ATCC CRL-11605), which is known as a rat insulinoma cell and has a GLP-1 receptor, thereby being generally used for measurement of in-vitro activity of GLP-1. RIN-m5F cells were treated with GLP-1, native exendin-4, and exendin-4 derivatives including N-terminal-α-desamino-histidyl-Exendin-4 at varying concentrations, and then cAMP production due to the test materials was examined to determine $EC_{50}$ values.

TABLE 1

| test materials | $EC_{50}$ (nM) | ratio vs Exendin4 |
|---|---|---|
| Exendin-4 | 1.21 | 100 |
| Desamino-histidyl(DA)-Exendin-4 | 0.95 | 127.4 |
| Dimethyl-histidyl(DM)-Exendin-4 | 1.31 | 92.4 |
| imidazoacetyl(CA)-exendin-4 | 1.2 | 100 |
| beta-hydroxypropionyl(HY)-exendin-4 | 1.3 | 92.4 |

Example 3

Measurement of Insulinotropic Activity of Exendin-4 Derivative

The insulinotropic activities of exendin-4 derivatives were compared in RINm5F cells. RINm5F cells were thawed, and subcultured at least once, followed by inoculation into 96-well plates at a density of $1 \times 10^5$ cells/well with culture media containing FBS (Gibco, #11082). Then, the cells were cultured in a 5% $CO_2$ incubator at 37° C. for 48 hrs. The culture media were replaced with fresh media containing 0.5% FBS, and then incubated for 1 hr. Each of CA-exendin-4 and exendin-4 (byetta, Amylin) was diluted with culture media containing 0.5% FBS and glucose to yield concentrations from 10 nM to 0.001 nM. Except for the exendin samples, diluted solutions were prepared, and used as a control group. The culture media of RINm5F cells were removed, and the prepared samples were added thereto, followed by culturing in a 5% $CO_2$ incubator at 37° C. for 1 hr. Then, the media were recovered from each well. A rat insulin ELISA kit (Mercodia) was used to determine the insulin concentrations of the recovered media, and the results are shown in FIG. 2 and Table 2.

TABLE 2

| Sample | Ratio of max insulin secretion to control group |
|---|---|
| CA Exendin-4 | 83.6% |
| Exendin-4 | 43.3% |

As shown in FIG. 2 and Table 2, it was found that one of exendin-4 derivatives, CA exendin-4 exhibited about 2-fold higher insulinotropic activity than native exendin-4 at the same concentration.

Example 3

Comparison of In Vivo Efficacy of Exendin-4 Derivative

To measure in vivo efficacy of exendin-4 derivatives, their blood glucose lowering effect was measured in diabetic animal model, as compared with native exendin-4. The db/db mice (Jackson Lab, 10-12 week-old) were fasted for 2 hrs, and then administered with exendin-4 and CA exendin-4 at an amount of 0.01-1000 mcg·kg, respectively. After 1 hr, blood samples were collected from tail blood vessel to measure blood glucose levels using a glucometer. Exendin-4, CA exendin-4, and vehicle were administered via subcutaneous route, and % change of blood glucose vs the vehicle was calculated at each concentration. At each concentration, the $ED_{50}$ for the blood glucose lowering effect was calculated using Prism program (FIG. 3, Table 3).

TABLE 3

| Sample | $ED_{50}$ (mcg/kg) | $R^2$ |
|---|---|---|
| CA exendin-4 | 2.30 | 0.99 |
| Exendin-4 | 9.92 | 0.98 |

As shown in FIG. 3 and Table 3, it was found that CA exendin-4 exhibited about 5-fold higher blood glucose lowering effect than native exendin-4 in the diabetic animal model.

INDUSTRIAL APPLICABILITY

The insulinotropic peptide derivatives according to the present invention maximize the intrinsic insulinotropic activity of exendin, that is, a therapeutic effect on type 2 diabetes, and induce reduction of food intake, delay in gastric emptying or the like, being superior to native and other insulinotropic peptide analogs. Therefore, the insulinotropic peptide derivatives and the pharmaceutical composition comprising the same according to the present invention can be effectively provided for the treatment of the diseases.

What is claimed is:

1. A modified exendin-4, wherein the N-terminal histidine residue of a native exendin-4 is substituted with a residue selected from the group consisting of N-dimethyl-histidyl, beta-hydroxy imidazopropionyl, 4-imidazoacetyl and beta-carboxy imidazopropionyl.

2. The modified exendin-4 as set forth in claim 1, wherein the modified exendin-4 consists of an amino acid sequence of the following Formula 1:

R1-X—R2 wherein R1 is selected from the group consisting of N-dimethyl-histidyl, beta-hydroxy imidazopropionyl, 4-imidazoacetyl and beta-carboxy imidazopropionyl;

R2 is selected from the group consisting of —NH$_2$ or —OH;

X is Gly-Glu-Gly-Thr-Phe-Thr-Ser-Asp-Leu-Ser-Y-Gln-Met-Glu-Glu-Glu-Ala-Val-Arg-Leu-Phe-Ile-Glu-Trp-Leu-Z-Asn-Gly-Gly-Pro-Ser-Ser-Gly-Ala-Pro-Pro-Pro-Ser or Gly-Glu-Gly-Thr-Phe-Thr-Ser-Asp-Leu-Ser-Y-Gln-Met-Glu-Glu-Glu-Ala-Val-Arg-Leu-Phe-Ile-Glu-Trp-Leu-Z-Asn-Gly-Gly;

Y is selected from the group consisting of Lys, Ser, and Arg; and

Z is selected from the group consisting of Lys, Ser, and Arg.

3. The modified exendin-4 as set forth in claim 2, wherein R1 is N-dimethyl-histidyl, Y is Lys or Ser, Z is Lys, and R2 is —NH$_2$.

4. The modified exendin-4 as set forth in claim 2, wherein R1 is 4-imidazoacetyl, Y is Lys or Ser, Z is Lys, and R2 is —NH$_2$.

5. The modified exendin-4 as set forth in claim 2, wherein R1 is beta-hydroxy imidazopropionyl, Y is Lys or Ser, Z is Lys, and R2 is —NH$_2$.

6. The modified exendin-4 as set forth in claim 2, wherein R1 is beta-carboxy imidazopropionyl, Y is Lys or Ser, Z is Lys, and R2 is —NH$_2$.

7. A pharmaceutical composition comprising the modified exendin-4 of claim 1 and a pharmaceutically acceptable carrier.

8. A pharmaceutical composition comprising the modified exendin-4 of claim 2 and a pharmaceutically acceptable carrier.

* * * * *

```
SEQUENCE LISTING

<160> NUMBER OF SEQ ID NOS: 3

<210> SEQ ID NO 1
<211> LENGTH: 38
<212> TYPE: PRT
<213> ORGANISM: artificial
<220> FEATURE:
<223> OTHER INFORMATION: Synthetic construct
<220> FEATURE:
<222> LOCATION: 11..11
<223> OTHER INFORMATION: Lys, Ser, or Arg
<220> FEATURE:
<222> LOCATION: 26..26
<223> OTHER INFORMATION: Lys, Ser, or Arg

<400> SEQUENCE: 1

Gly Glu Gly Thr Phe Thr Ser Asp Leu Ser Xaa Gln Met Glu Glu Glu
1               5                   10                  15

Ala Val Arg Leu Phe Ile Glu Trp Leu Xaa Asn Gly Gly Pro Ser Ser
            20                  25                  30

Gly Ala Pro Pro Pro Ser
        35

<210> SEQ ID NO 2
<211> LENGTH: 29
<212> TYPE: PRT
<213> ORGANISM: artificial
<220> FEATURE:
<223> OTHER INFORMATION: Synthetic construct
<220> FEATURE:
<222> LOCATION: 11..11
<223> OTHER INFORMATION: Lys, Ser, or Arg
<220> FEATURE:
<222> LOCATION: 26..26
<223> OTHER INFORMATION: Lys, Ser, or Arg

<400> SEQUENCE: 2

Gly Glu Gly Thr Phe Thr Ser Asp Leu Ser Xaa Gln Met Glu Glu Glu
```

```
1               5                   10                  15
Ala Val Arg Leu Phe Ile Glu Trp Leu Xaa Asn Gly Gly
            20                  25

<210> SEQ ID NO 3
<211> LENGTH: 38
<212> TYPE: PRT
<213> ORGANISM: artificial
<220> FEATURE:
<223> OTHER INFORMATION: Synthetic construct
<220> FEATURE:
<222> LOCATION: 11..11
<223> OTHER INFORMATION: Lys, Ser, or Arg
<220> FEATURE:
<222> LOCATION: 26..26
<223> OTHER INFORMATION: Lys, Ser, or Arg

<400> SEQUENCE: 3

Ser Asp Gly Thr Phe Thr Ser Asp Leu Ser Xaa Gln Met Glu Glu Glu
1               5                   10                  15

Ala Val Arg Leu Phe Ile Glu Trp Leu Xaa Asn Gly Gly Pro Ser Ser
            20                  25                  30

Gly Ala Pro Pro Pro Ser
            35
```